United States Patent
Stjernschantz et al.

(10) Patent No.: US 6,562,868 B1
(45) Date of Patent: May 13, 2003

(54) METHOD FOR TREATMENT OF FEMALE SEXUAL DYSFUNCTION

(75) Inventors: Johan Stjernschantz, Uppsala (SE); Bahram Resul, Uppsala (SE)

(73) Assignee: Synphora AB, Uppsala (SE)

( * ) Notice: Subject to any disclaimer, the term of this patent is extended or adjusted under 35 U.S.C. 154(b) by 0 days.

(21) Appl. No.: 09/869,431

(22) PCT Filed: Jan. 4, 2000

(86) PCT No.: PCT/SE00/00006

§ 371 (c)(1),
(2), (4) Date: Jun. 28, 2001

(87) PCT Pub. No.: WO00/40248

PCT Pub. Date: Jul. 13, 2000

(30) Foreign Application Priority Data

Jan. 8, 1999 (SE) .............................................. 9900025

(51) Int. Cl.$^7$ .............................................. H01N 37/08
(52) U.S. Cl. ...................... 514/530; 514/559; 514/573
(58) Field of Search ................ 514/530, 573, 514/559

(56) References Cited

U.S. PATENT DOCUMENTS

| 4,054,595 | A | * | 10/1977 | Marx et al. | 560/121 |
|---|---|---|---|---|---|
| 4,140,712 | A | * | 2/1979 | Hayashi et al. | 562/503 |
| 4,164,446 | A | | 8/1979 | Marx et al. | |
| 4,190,670 | A | * | 2/1980 | Marx et al. | 424/305 |
| 5,698,598 | A | * | 12/1997 | Woodward | 514/530 |
| 5,877,211 | A | * | 3/1999 | Woodward | 514/530 |
| 2002/0004529 | A1 | * | 1/2002 | Neal | 514/573 |

FOREIGN PATENT DOCUMENTS

| GB | 1488006 | | 10/1977 |
|---|---|---|---|
| WO | 99/02164 | | 1/1999 |
| WO | WO 99/20266 | * | 4/1999 |
| WO | 99/21562 | | 5/1999 |

OTHER PUBLICATIONS

Chemical Abstracts, vol. 87, No. 7, Aug. 15, 1977, (Columbus, Ohio, USA), Spilman, C.H., et al., "Effects of 19–hydroyprostaglandins on oviductal and uterine motility", p. 58, The Abstract No. 48352q, Prostaglandins 1977, 13(4), 795–805.

Chemical Sbstracts, vol. 20, No. 1, Jan. 3, 1994, (Columbus, Ohio USA), Woodward, D.F. et al., "Identification of 19(R)–OH prostaglandin E2 as a selective prostanoid EP2–receptor agonist", p. 161, The Abstract No. 1279f, Prostaglandins 1993, 46 (4), 371–383.

* cited by examiner

Primary Examiner—Zohreh Fay
Assistant Examiner—Brian-Yong S. Kwon
(74) Attorney, Agent, or Firm—Banner & Witcoff, Ltd.

(57) ABSTRACT

A selective $EP_2$ or $EP_4$ prostanoid receptor agonist can be used to treat female sexual dysfunction. Salts and esters of the agonists can also be used. Formulations comprising such agonists, salts, or esters can be in the form of a cream, gel, ointment, or solid, useful for topical administration.

4 Claims, 2 Drawing Sheets

METHOD FOR TREATMENT OF FEMALE SEXUAL DYSFUNCTION

This is a U.S. National Phase Application Under 35 U.S.C. §371 of PCT/SE00/00006 filed Jan. 4, 2000, and claims the priority of Application No. 9900025-9 filed in Sweden on Jan. 8, 1999.

FIELD OF INVENTION

The present invention relates to the treatment of female sexual dysfunction, and more particularly to a novel prostaglandin based composition therefore and the use thereof for treating female sexual dysfunction.

BACKGROUND OF THE INVENTION

Female sexual dysfunction is not a well defined clinical entity, but can be characterized as the equivalence of male erectile dysfunction i.e. the inability of the female to reach sexual satisfaction. In contrast to the mechanism and etiology of male erectile dysfunction which have been extensively studied, only little is known about female sexual dysfunction; however, a reasonable hypothesis is inadequate vasodilatory capacity of the external genitals. Thus local drugs that restore the vasodilatory capacity of the genitals to the appropriate stimuli can be anticipated to improve the female sexual function. The prevalence of female sexual dysfunction is largely unknown, and dependent on age, but generally it can be estimated that such dysfunction is common e.g. amongst post menopausal women. Currently there is no adequate treatment of female sexual dysfunction other than hormonal treatment in post menopausal women.

While it is understood that many drugs with vasodilatory capacity administered e.g. orally may have effect on the genitals, and that certain systemic drugs e.g. sildenafil used for male erectile dysfunction, may have beneficial effect also for the treatment of female sexual dysfunction, it is a clear advantage if the drugs can be administered locally in the genital tract to avoid systemic side-effects.

SUMMARY OF THE INVENTION

We have now unexpectedly found that certain prostaglandin analogues of the E-type, more specifically agonists of the $EP_2$ prostanoid receptor, exert good relaxant effect in the penile cavernous tissue, and in blood vessels while exhibiting markedly reduced pain inducing effect typical for many prostaglandins. Since the female external genitals embryologically correspond to the male genitals such as the penis, and expansive cavernous tissue is present in the genitals of both sexes it is very likely that the effect of certain prostaglandin analogues is fundamentally similar in the male and female. Such drugs may therefore also be used to treat female sexual dysfunction.

In particular we have found that $PGE_2$ analogues substituted in carbon 18, 19 or 20 with hydroxyl (OH) exert beneficial effect, and especially one analogue, namely 19R-OH-$PGE_2$, exhibited a surprisingly advantageous effect with respect to relaxation of cavernous tissue and blood vessels without inducing pain as studied in an animal model.

Thus, in a first aspect, the present invention provides a composition for the treatment of female sexual dysfunction, comprising a prostaglandin which is a selective $EP_2$ or $EP_4$ receptor agonist, or an active derivative, including the free acid, or a salt or an ester thereof, optionally together with a physiologically acceptable carrier or vehicle.

In a second aspect, the invention provides a method of treating female sexual dysfunction, which method comprises administering a therapeutically active and physiologically acceptable amount of the composition to an individual in need thereof.

In a third aspect, the invention provides the use of a selective $EP_2$ or $EP_4$ receptor agonist, or an active derivative including the free acid, a salt or an ester thereof, for the preparation of a medicament for the treatment of female sexual dysfunction.

DETAILED DESCRIPTION OF THE INVENTION

Engorgement of the genital tissue is primarily based on marked relaxation of both arteries and cavernous tissue as demonstrated e.g. in the penis. $PGE_1$ and the $EP_2$ receptor agonists cause vasodilation and relax the expansive tissue to about the same extent and thus promote an erectile response. However, $PGE_1$ being a natural prostaglandin with low selectivity for a specific prostanoid receptor has a marked irritant effect and causes pain as evident in clinical trials performed with alprostadil e.g. Padha-Natham, 1997) and as will also be shown in the experimental part further below. According to the invention, however, prostaglandin analogues with selectivity primarily for the $EP_2$ receptor which induce the same beneficial effect but with significantly less irritant effect are much more preferable as it can be predicted that such analogues will cause no or only minimal pain in clinical practice. To facilitate the understanding of the invention, a general description of prostaglandins is first given.

The prostaglandins are fatty acids usually derived from the precursors eicosatrienoic, eicosatetraenoic or eicosapentaneoic acid through metabolic steps involving oxygenation. The prostaglandins typically carry a cyclopentane ring to which two carbon chains link, the upper chain usually being called the alpha chain and the lower the omega chain. The alpha chain is a 7 carbon chain with a terminal carboxylic acid moiety whereas the omega chain is an 8 carbon methyl-terminated aliphatic chain. Depending on the number of double bonds in these chains subscripts of 1–3 are used. In prostaglandins with subscript 1, e.g. $PGE_1$, the double bond is situated between carbons 13 and 14 in the omega chain, and it exhibits trans configuration in naturally occuring prostaglandins. In prostaglandins with subscript 2, e.g. $PGE_2$, an additional double bond in the cis configuration exists between carbons 5 and 6 in the alpha chain, and finally in prostaglandins with subscript 3 a third double bond is situated between carbons 17 and 18 in the omega chain. This double bond also exhibits cis configuration in naturally occuring prostaglandins. All naturally occuring prostaglandins carry a hydroxyl group in carbon 15, which is essential for biological activity. The substituents and the configuration of the cyclopentane ring determine whether the prostaglandin is of the A, B, C, D, E, F, G, H, I or J type as depicted in Scheme 1 below. The prostaglandins that have been used to exemplify the present invention are of the E-type, and the chemical structures of these prostanoids are depicted in Scheme 2. Except for 18RS-OH-$PGE_2$-methyl ester the prostaglandin analogues were also used as acids.

Scheme 1

Scheme 2

The prostaglandins exert their pharmacologic effect through specific G protein coupled membrane receptors. There are at least 8 different receptors for the endogenous prostaglandins, namely the FP (PGF$_{2\alpha}$), EP$_1$, EP$_2$, EP$_3$, EP$_4$ (PGE$_2$), DP (PGD$_2$), IP (PGI$_2$), and TP (TxA$_2$) receptors, the most common naturally occuring ligand for respective receptor being shown within parentheses. At least for the EP$_3$ receptor splice variants have been shown to exist. The EP$_2$ and EP$_4$ receptors are closely related, and probably mediate similar effects. We have therefore studied the effect only on the EP$_2$ receptor, and regard it to represent the EP$_4$ receptors as well in the case the compounds studied would have an effect on that receptor, too. The molecular biology and pharmacology of the prostanoid receptors have recently been reviewed by Coleman et al., 1994.

From a therapeutic point of view a problem with the endogenous prostaglandins is that they exert effects on many different prostanoid receptors. Each endogenous prostaglandin has a preference for one specific receptor type, but is not very selective and usually distinguishes poorly between the receptor subtypes, i.e. the EP receptors. Thus PGE$_1$ and PGE$_2$ are good ligands for all subtypes of the EP receptor. Consequently selective effects on one of the subtypes of the EP receptor is impossible to achieve with the endogenous prostaglandins. However, certain synthetic prostaglandin analogues, e.g. butaprost, 11-deoxy-PGE$_1$ and AH13205 as well as a naturally occuring metabolite of PGE$_2$, namely 19R-OH-PGE$_2$, are selective EP$_2$ prostanoid receptor agonists.

18-OH-PGE$_2$, 19R-OH-PGE$_2$ and 20-OH-PGE$_2$ are effective EP$_2$ receptor agonists with selectivity for the EP$_2$ receptor over the EP$_3$ receptor. The endogenous PGE$_1$ is unselective and does not distinguish between the EP receptor subtypes sufficiently, and furthermore significantly spills over on the DP/IP receptors which e.g. the 18-, 19- and 20-OH substituted PGE$_2$ analogues do not. However, PGE$_1$ has been included as a reference substance as it is the only prostaglandin currently in clinical use for the treatment of erectile dysfunction.

Accordingly, high selectivity or specificity to the EP$_2$ receptor compared to other prostaglandin receptors, particularly the EP$_3$ receptor, characterizes the compounds to be used in the method or compositions according to the present invention. It need not be said that the more specific the compound is for the EP$_2$ receptor the better results are obtained, but a certain advantage is, of course, achieved also in cases of some interaction with other receptors. High selectivity in this connection means that the effect on the EP$_2$ receptor is at least more than 5 times, especially more than 10 times, and in particular more than 100 or 1000 times the effect on other prostaglandin receptors.

As stated above, according to the present invention, in particular the selective EP$_2$ receptor agonist 19R-OH-PGE$_2$ and its carboxylic acid esters appear to be unique and ideally suited for the treatment of female sexual dysfunction. In this context it should be mentioned that 19R-OH-PGE$_2$ is a metabolite of PGE2 in the genital tract and can be found in large quantities normally in human semen (Taylor and Kelly, 1974). However, the physiological role of this unique metabolite is unknown. Thus, 19R-OH-PGE$_2$ and its carboxylic acid esters constitute a very attractive medication for female sexual dysfunction since this analogue has a marked vasodilatory capacity, causes no pain, and furthermore occurs normally in the body.

With respect to 19R-OH-PGE$_2$ which appears ideally suited for treatment of female sexual dysfunction, it should be observed that various modifications or substitutions of the molecule are possible as long as the new derivatives exhibit selective agonism on the EP$_2$ receptor.

In Formula I, the wavy bonds represent the α (S) or β (R) configuration, and the dashed bonds represent a single, a triple or a double bond in the cis or trans configuration. R in the formula is hydrogen, a salt moiety, e.g. an alkali or ammonium salt, a straight or branched saturated or unsaturated alkyl group, preferably with 1–10 carbons, an alicyclic ring, preferably with 3–8 carbons, arylalkyl, preferably aryl-$C_{2-5}$ alkyl, or an aryl ring. X is a straight chain, saturated or unsaturated, preferably consisting of 2–5 carbons optionally interrupted by a heteroatom (O, S, N), and the chain may contain an alicyclic ring, preferably C3–C7 cycloalkyl, or an aryl or heteroaryl ring. R1 and R2, which are identical or different, are hydrogen, hydroxy, halogen, oxygen (=O or alkoxy) or an alkyl group with 1–3 carbons or analkoxy group with 1–3 carbons or an ester OCOR3, where R3 is a straight or branched, saturated or unsaturated alkyl group preferably containing 1–10, especially 1–6 carbons, or a cycloalkyl, preferably containing 3–7 carbons, or an aryl or arylalkyl group, preferably aryl-$C_{2-5}$ alkyl (e.g. benzyl). Optionally C10 can be substituted e.g. to contain a mono- or dialkyl group.

Z is an alkyl chain of 1–8, e.g. 3–8 and 2–4 carbons, saturated or unsaturated, optionally interrupted by one or more heteroatoms (O, S, N), and containing one or more, preferably one substituent Y, attached to a carbon atom within the chain or a carbon atom in terminal position. The chain Z may be branched, containing alkyl (preferably methyl) substituents and/or contain an alicyclic ring, e.g. a cycloalkyl, or an aryl (esp. a benzene) or heteroaryl ring, in inter- or terminal position. Y, is hydroxy, sulfhydryl, amino, methylamino, dimethylamino, $C_{1-3}$ alkoxy or halogen (Cl, Br, F) or oxygen (keto). In a preferred embodiment of the invention Y is attached to carbon 18, 19 or 20. In the most preferred embodiment Y is OH and attached to carbon 19. At present it is believed that the inventive concept is based on the electronegative effect introduced by Y.

I

The prostaglandins may be epimeric mixtures as well as in the form of the individual epimers.

Description of Suitable Embodiments

The $EP_2$ prostanoid receptor agonists according to the present invention can be used as the normal carboxylic acids, salts (e.g. cationic) or as ester prodrugs, preferentially as carboxylic acid esters. The active compound can be administered topically in a pharmaceutically acceptable delivery medium. Cyclodextrins may be employed for solubilisation and stabilisation. Different delivery media, e.g. liniment, creams, gels, ointments, and possibly solid state forms may be employed. Gels, creams, ointments and solid state formulations may or may not contain preservative such as benzalkonium chloride, chlorhexdine, thiomersal, parabenzoic acid, and other compounds with satisfactory antimicrobial effect. The dose interval is 0.001–1 mg, typically 0.01–0.1 mg per application.

Accordingly the new medicament should be administered locally in the genital tract. Such treatment should be initiated 5–60 min before intercourse.

Exemplification of the Invention

The test compounds $PGE_1$-isopropyl ester, 18RS-hydroxy-$PGE_2$-methyl ester, 19R-hydroxy-$PG_2$-methyl ester and 20-hydroxy-$PGE_2$-methyl ester were dissolved in 0.5% polysorbate-80 as a stock solution, and were diluted in 0.5% polysorbate-80 to the appropriate concentrations in the various pharmacological experiments.

Synthesis of $PGE_1$-isopropyl ester $PGE_1$ was obtained from Chinoin, Pharmaceutical and Chemical Works Co. Ltd., Budapest, Hungary.

DBU (644 mg, 4.2 mmol) in acetonitrile (1 ml) was added dropwise to a stirred solution of $PGE_1$ (300 mg, 0.84 mmol) in actonitrile (3 ml) at 0° C. The mixture was allowed to warm to room temperature whereupon isopropyl iodide (1142 mg, 6.72 mmol) in acetonitrile (2 ml) was added dropwise. After being stirred for 10 h (TLC monitoring), the reaction mixture was quenched with water (8 ml), the mixture was extracted with ethyl acetate (2×50 ml), and the extract was washed with brine (10 ml), citric acid 3% (10 ml), and finally sodium hydrogen carbonate 5% (2×10 ml). After drying with anhydrous sodium sulphate, the solvent was removed in vacuo and the residual oil was chromatographed on silicagel using ethyl acetate as eluent. This afforded 230 mg of the product (69%) of the title compound as a colorless oil: $R_f$=0.18 (ethyl acetate); $^1$H NMR (CDCl3) δ0.89 (m, 3H), 1.2 (d, 6H), 1.21–1.4 (m, 10H), 1.42–1.62 (dm, 6H), 2.2–2.4 (dm, 4H), 2.7–2.75 (dd, 1H), 4.0–4.17 (dm, 2H), 5.0 (m, 1H), 5.5–5.7 (dm, 2H).

Synthesis of 18RS-hydroxy-$PGE_2$-methyl ester

1. Preparation of Dimethyl-(2-oxo-5-heptyne)-phosphonate.(2)

To a stirred suspension of dry sodium hydride (3.13 g, 124.07 mmol) in dry THF (100 ml) at room temperature was added dropwise a solution of dimethyl 2-oxopropyl)-phosphonate (20.61 g, 124.07 mmol) in dry THF (50 ml) under $N_2$. The reaction mixture was stirred for 1 h, then cooled in an ice-bath and treated with a solution of n-butyllithium (7.95 g, 124.07 mmol) in hexane, causing a dark brown solution to be formed. Stirring was continued for 1 h at 0° C., followed by dropwise addition of 1-bromo2-butyne.1 (15 g, 112.79 mmol) in THF (30 ml). The reaction mixture was gradually warmed to room temperature and after 1 h (TLC monitoring) the reaction mixture was quenched with ice-water, HCl 1M to pH about 4 and extracted, twice, with ethyl acetate. The organic layer was washed with brine and chromatographed on silica gel using EtOAc as eluent. Rf=0.38 (silica gel, ethylacetate), yield 18 g (73%).

2. (1S,5R,6R,7R)-6-Formuyl-7-{(4-phenylbenzoyl)oxy}-2-oxabicyclo{3.3.0}octan-3-one.(3)

A mixture of Coreys lactone (23.06 g, 65.44 mmol)), DCC (40.50 g, 196.31 mmol)), DMSO (27.8 ml, 392.6 mmol) and phosphoric acid 85% (2.2 ml) in DME (130 ml) was stirred at room temperature for 2 h (TLC monitoring). The precipitate was removed on silica-gel pad washed with DME (2×50 ml). The filtrate was concentrated in vacuo and used for the next step without isolation.

4. (1S,5R,6R,7R)-6-(3-Oxo-6-yn-1E-1-octenyl)-7-{(4-phenylbenzoyl)oxy}-2-oxabicyclo{3.3.0}octan-3-one.(4)

To a stirred suspension of sodium hydride (1.98 g, 78.53 mmol)) in DME (140 ml) under $N_2$ was added dropwise the above phosphonate 2 (18.56 g, 85.07 mmol) and stirred mechanically at room temperature for 1.5 h. The mixture was then cooled to −5° C., and a solution of the above crude Coreys aldehyde 3 was added dropwise. After 30 min at 0°

C. and 2 h at room temperature (TLC monitoring), the reaction mixture was neutralised with citric acid 5% and extraced with ethyl acetate (2×100 ml). The organic layer was dried and evaporated. The residue (oil) was chromatographed on silica-gel using ethyl acetate and 10% methanol in ethyl acetate successively, giving a light yellowish oil. $R_f=0.58$(silica-gel, ethyl acetate), yield 52%.

5. (1S,5R,6R,7R)-6-(3,6-Dioxo-1E-1-octenyl)-7-{(4-phenylbenzoyl)oxy}-2-xabicyclo{3.3.0}octan-3-one. (5)

To the acetylenic solution 4 in acetonitrile:water 2:1 (100 ml) was added mercuric oxide (13.8 g, 63.73 mmol)) and sulfuric acid 1M (25.49 ml, 25.49 mmol)). The reaction mixture was stirred magnetically. After about 1 h at room temperature (TLC monitoring) the reaction mixture was worked-up by addition of ethylacetate and HCl 1M. The organic layer was dried and evaporated. The crude oil was used for the next step without purification. $R_f=0.44$ (silicagel, EtOAc), yield=41%.

6. (1S,5R,6R,7R)-6-(3RS,6RS-Dihydroxy-1E-1-octenyl)-7-{(4-phenylbenzoyl)oxy}-2-oxabicyclo{3.3.0}octan-3-one.(6)

To a stirred solution of the above diketone 5 (12.0 g, 26.1 mmol) and cerium chloride hepta hydrate (5.83 g, 15.64 mmol) at −20° C. in methanol:methylene chlorider 1:1 was added sodium borohydride (1.48 g, 39.09 mmol)) in small portions under $N_2$. After 30 min (TLC monitoring). The reaction mixture was quenched with HCl 1M to pH about 4–5, and diluted with water (50 ml) and ethyl acetate (100 ml). The organic layer was separated and the water layer was washed twice with EtOAc, dried and evaporated. The residue was purified on silica gel using EtOAc as eluent. The title compound 6 was obtained as colorless oil: yield 8.8 g (71%). $R_f=0.15, 0.13$ corresponding to the two isomers 15α and 15β (silicagel EtOAc).

$^1$H NMR (CDCl$_3$) δ0.9 (m, 3H), 1.4–1.8 (dm, 6H), 2.3 (d, 1H), 2.5–2.9 (dm, 5H), 3.5 (m, 1H), 4.2 (m, 1H). 5.1 (m, 1H), 5.3 (m, 1H), 5.7 (m, 2H), 7.4 (m, 1H), 7.5 (m, 2H), 7.6–7.7 (dd, 4H), 8.1 (d, 2H); $^{13}$C NMR (CDCL$_3$) d 176.40 (C6H4C=O), 16591 (lactone C=O), 146.07, 139.83, 136.21, 130.15, 128.91, 128.31, 127.15, 83.27, 79.13, 73.11, 71.79, 71.48, 54.08, 42.84, 42.75, 37.55, 34.85, 34.01, 33.43, 32.95, 32.09, 30.17, 9.96.

7. (1S,5R,6R,7R)-6-(3RS,6RS-Di t butyldimethylsilyloxy-1E-1-octenyl)-7{(4-phenylbenzoyl)oxy}-2-oxabicyclo{3.3.0}octan-3-one.(7)

To a stirred solution of the above dihydroxy compound 6 (8.6 g, 18.51 mmol) in dichloromethane was added triethyl amine (12.83 ml, 92.56 mmol)), t-butyldimethylsilyl chloride (13.95 g, 92.56 mmol)) and 4-dimethylamino pyridine (1.13 g, 9.26 mmol). The mixture was stirred magnetically for 15 h at room temperature. The reaction mixture was diluted with ether, filtered and the precipitate was washed with ether. The organic layer was washed with brine, dried and concentrated in vacuo. The residue was chromatographed on silica gel using 5% ether in dichloromethane. $R_f=0.58$ (silica gel, 5% ether in CH2Cl2). Yield 12.2 g (92%).

8. (1S,5R,6R,7)-6-(3RS,6RS-Di t butyldimethylsilyloxy-1E-1-octenyl)-7-{(4-hydroxyl}-2-oxabicyclo{3.3.0}octan-3-one.(8)

To a stirred solution of the above disilyl ether 7 (12 g, 17.31 mmol) in methanol was added potassium carbonate (1.2 g, 8.66 mmol). The reaction mixture was stirred at room temperature for 4 h (TLC monitoring). The mixture was neutralised with citric acid 5%, extracted twice with ethyl acetate (100 ml), dried and concentrated in vacuo. The oil was chromatographed on silica gel using gradient elution with 5% ether in CH$_2$Cl$_2$ and EtOAc:acetone 1:1 successively. $R_f=0.43$ (silica gel, ethyl acetate), yield=8.86 g (74%).

9. (1S,5R,6R,7R)-6-(3RS,6RS-Di t butyldimethylsilyloxy-1E-octenyl)-7-{(4-t-butyldimethylsilyloxy}-2-oxabicyclo{3.3.0}octan-3-one.(9)

To a stirred solution of the above dislyloxy ether 8 (6.6 g, 12.86 mmol) in CH$_2$Cl$_2$ at room temperature was added triethyl amine (7.14 ml, 51.47 mmol) t-butyldimethylsilyl chloride (7.76 g, 51.47 mmol) and 4-diethyl aminopyridine (0.47 g, 3.9 mmol). The reaction mixture was worked-up as in 7. The crude product was chromatographed on silica gel using 5% ether in dichloromethane to give a pure trisilyloxy ether product 9 as an oil. $R_f=0.62$ (silica gel, 5% ether in CH$_2$Cl$_2$), yield 7.8 g, (96%).

10. (1S,5R,6R,7R)-6-(3RS,6RS-Di t butyldimethylsilyloxy-1E-1-octenyl)-7-{(4-t-butyldimethylsilyloxy}-2-oxabicyclo{3.3.0}octan-3-ol.(10)

A solution of diisobutyl aluminium hydride (DIBAL-H) (2.9 g, 20.87 mmol) in dry THF was added dropwise to a stirred solution of the above trisilyl ether lactone 9 (7.7 g, 12.24 mmol) in THF (80 ml) at −72/−80° C. After 1 h (TLC monitoring), the reaction mixture was quenched with ice (15 g) and ethyl acetate (150 ml), filtered and the filtrate was concentrated in vacuo. The residue was used directly without separation in the next step. $R_f=0.27$ (Silica gel, 5% ether in dichloromethane).

11. 11,15RS,18RS-Tri-t-butyldimethylsilyloxy-PGF$_{2\alpha}$(11)

To a stirred suspension of 4-carboxybutyl-triphenylphosphonium bromide (21.70 g, 48.95 mmol) in dry THF under $N_2$ at −5° C. was added potassium tert-butoxide (10.99 g, 97.91 mmol) and the mixture was stirred at room temperature for 30 min. To the resultant red-orange solution of ylide at −15/−10° C. was added the lactol 10 (7.7 g, 12.24 mmol) in THF, and the mixture was stirred for 2–3 h (TLC monitoring) at room temperature. The reaction mixture was diluted with water and quenched with citric acid 15% to pH 6–7 and extracted with EtOAc, dried and concentrated in vacuo. The resultant slurry was used directly without isolation for the next step.

12. 11,15,18RS-Tri-t-butyldimethylsilyloxy-PGF$_{2\alpha}$ methyl ester (12)

Methyl iodide (8.6 g, 61.20 mmol), was added to a stirred solution of the crude product 10 (8.73 g, 12.24 mmol) and N,N-Diisopropyl ethyl amine (9.473 g, 73.44 mmol) in acetonitrile at room temperature. After 15 h (TLC monitoring) the mixture was diluted with water (100 ml) and ethyl acetate (150 ml), washed with sodium hydrogen carbonate 5% (60 ml) and brine (70 ml). The organic layer was dried and evaporated in vacuo. The residue was chromatographed on silica gel using EtOAc as eluent. $R_f=0.18$ (silica gel, EtOAc:hexane 1:9).

13. 11,15,18RS-Tri-t-butyldimethylsilyloxy-PGE$_2$ methyl ester (13)

To a stirred solution of the compound 11 (3.3 g, 4.54 mmol) in dichloromethanne was added pyridinium chlorchromate (PCC).(3.9 g, 18.15 mmol) treated with aluminium oxide (1 g PCC was stirred with 5 g aluminium oxide in acetone, the solvent was removed in vacuo giving a light yellow powder). The resulting suspension was stirred at room temperature for 4 h (TLC monitoring). The suspension was filtered on silica gel pad, washed with dichloromethane. The solvent was removed and the resulting oil was diluted with ether and washed with water (50 ml), sodium hydrogen carbonate 5% (50 ml). The solvent was removed in vacuo. The residue was chromatographed on silica gel using 5% ether in $CH_2Cl_2$. $R_f$=0.32 (silica gel, EtOAc:hexane 1:9), yield 3.1 g (86%).

14. 18RS-hydroxy $PGE_2$ methyl ester (14)

The protecting groups 11,15,18-tri-t-butyldimethylsilyl chloride were removed by addition of HF 4% (108 ml) to a solution of 13 (3.0 g, 3.98 mmol) in acetonitrile (300 ml). The reaction mixture was stirred at room temperature for about 8 h (TLC monitoring). The reaction mixture was worked-up by addition of EtOAc (200 ml). The organic layer was separated and washed with sodium bicarbonate 5% and the pH was adjusted to about 6. The organic layer was washed with brine, dried and concentrated in vacuo. The residue was purified by column chromatography on silica gel using gradient elution with $CH_2Cl_2$, EtOAc and 5–10% methanol in ether successively (The stationary phase, silica gel, in the column must be washed with the eluent containing triethylamine before purification, to avoid isomerization) 18RS-hydroxy-15S-$PGE_2$ Me ester $R_f$=0.16 (5% MeOH in ether); yield 310 mg. 18RS-hydroxy-15R-$PGE_2$ Me ester $R_f$=0.20 (5% MeOH in ether); yield 248 mg.

18RS-hydroxy-$PGE_2$ methyl ester 1H NMR (CDCl3) δ0.9 (t, 3H), 1.4–1.7 (dm, 8H), 2.1 (m, 2H), 2.2 (m, 2H), 2.3–2.4 (m, 5H), 2.7 (m, 1H), 3.6 (m, 1H, 18-CHOH), 3.7 (s, 3H), 4.05, (m, 1H, 15-CHOH), 4.2 (m, 1H, 11-CHOH), 5.3–5.5 (dm, 2H, db), 5.6–5.8 (dm, 2H, db);

13C (NMR) δ214, 174.24, 136.7, 131.3, 130.8, 126.5, 72.36, 71.78, 71.70, 55.54, 54.54, 53.70, 51.60, 46.06, 34.06, 33.42, 33.00, 32.10, 30.34, 30.29, 30.07.

Scheme 3

Synthesis of 19-R-hydroxy-prostaglandin $E_2$-methyl ester 19R-hydroxy-prostaglandin $E_2$ was obtained from Cayman Chemicals, Ann Arbor, Mich., USA. Methyl iodide (9.2 mg, 0.065 mmol) in acetonitrile (1.0 ml) was added dropwise to a stirred solution of 19R-hydroxy-prostaglandin $E_2$ (4 mg, 0.011 mmol), and N,N-diisopropyl ethyl amine (7 mg, 0.054 mmol) in acetonitrile. More methyl iodide (4.5 mg, 0.032 mmol) in acetonitrile was added after 6 h and the stirring was continued for 12 h (TLC monitoring). The reaction mixture was quenched with water (5.0 ml) and extracted with ethyl acetate (2×10 ml), and the organic phase was washed with sodium hydrogen carbonate 5% (5 ml) and hydrochloric acid 0.5M (5 ml). After drying with an hydrous sodium sulphate, the solvent was removed in vacuo and the residue was chromatographed on silica-gel using ethyl acetate:acetone 1:1 and acetone as eluent. This afforded 3.2 mg (72.7%) of the product as a colorless oil: $R_f$=0.17 (ethyl acetate:acetone:acetic acid 1:1:0.01) $^1$H NMR (CDCl$_3$) δ1.25 (d, 3H), 1.5–1.7 (m, 8H), 2.1–2.6 (mm, 9H), 3.7 (s, 3H), 3.8 (m, 1H), 4.1 (m, 1H), 4.2 (m, 1H), 5.3–5.5 (dm, 2H), 5.6–5.8 (dm, 2H).

Synthesis of 20-OH-prostaglandin $E_2$-methyl ester

The commercially available 20-hydroxy PGE$_2$ (Cayman Chemicals, Ann Arbor, Mich.) (2.0 mg, 0.0054 mmol) was esterified in acetonitrile (2.0 ml) with methyl iodide (4.6 mg, 0.0327 mmol) in the presence of N,N-diisopropyl ethylamine (3.5 mg, 0.027mmol). The reaction mixture was stirred at room temperature for 10 h (TLC monitoring, silica gel, ethyl acetate). The reaction mixture was quenched with water. (3.0 ml) and extracted with ethyl acetate (2×10 ml). The organic layer was dried and concentrated in vacuo and the residual oil was chromatographed on silica gel using ethyl acetate:acetone 1:0.5 as eluent; $R_f$=0.38(silica gel, ethyl acetate:acetone 1:1).

Pharmacological Experiments

The effect of the test compounds on cavernous tissue was tested using penile tissue. As mentioned previously both in the male and female the genitals contain cavernous tissue, and the penile tissue can therefore be used as model for genital cavernous tissue. The general blood vessel relaxing effect of the test compounds was studied by investigating the immediate blood pressure decrease in rats upon intravenous infusion of the test compounds. The acute drop in blood pressure reflects a peripheral vasodilation in the animals brought about by the test compounds. The general irritative effect of the test compounds was studied in the cat eye which is very sensitive to noxious stimuli.

Human penile cavernous tissue was obtained fresh from surgery, and representative tissue samples were mounted in smooth muscle tissue baths containing a modified Kreb's solution consisting of NaCl 119 mM, KCl 4.6 mM, MgCl$_2$ 1.2 mM, NaH$_2$PO$_4$ 1.2 mM, NaHCO$_3$ 15 mM, CaCl$_2$ 1.5 mM and glucose 11 mM. The solution also contained indomethacin at a final concentration of about 3 μM. The solution was continuously bubbled by 95% O$_2$ and 5% CO$_2$, and the temperature was kept at 37° C.

The tissue preparations were stretched by a force corresponding to 500 mg, and were given a contractile tone by the addition of norepinephrine at a concentration of $10^{-6}$ M. Concentration-response curves were then constructed by adding cumulatively increasing concentrations of the prostaglandin analogues to the bath in a routine way. The relaxant effect was normalized by comparing to that of carbachol in the same preparation. PGE$_1$ and 19R-OH-PGE$_2$, respectively, were used as acids.

To study the effect of the PGE$_1$ and 19R-OH-PGE$_2$ on the penile vasculature, penile blood vessels of the rabbit were isolated and mounted as ring segments in a small vessel myograph (J.P. Trading, Denmark) containing a solution consisting of NaCl 119 mM, KCl 4.7 mM, CaCl$_2$ 1.5 mM, MgSO$_4$ 1.17 mM, KH$_2$PO$_4$ 1.18 mM, NaHCO$_3$ 25 mM, EDTA 0.027 mM and glucose 11 mM. The solution also contained indomethacin at a final concentration of about 3 μM, and was continuously bubbled by 95% O$_2$ and 5%CO$_2$. The temperature was kept constant at 37° C. The vessels were stretched and then precontracted using $10^{-6}$ M norepinephrine, and the vasorelaxant effect of the prostaglandin analogues was normalized by comparing it to that of papaverine in the same preparation. Cumulative concentration-response curves were constructed for the analogues.

The vasodilatory effect of the prostaglandin analogues was also studied in the rat by registering the blood pressure reducing effect. This is a relevant in vitro model for showing general vasodilatory effect of importance for inducing erection since vasodilation in penis is needed for achieving erection. Rats were anaesthetized with a mixture of ketamine and xylazin and the prostaglandin analogues were infused intravenously. The blood pressure was continuously registered in a femoral artery. Each analogue was infused in 3 escalating doses in the same animal. None of the compounds was found to have any significant effect of the heart rate and the immediate reduction in arterial blood pressure therefore reflects an acute vasodilatory response to the prostaglandin analogues tested. In all experiments the blood pressure reduction was transient and the blood pressure increased immediately after termination of the infusion. The analogues were used both as esters and acids for the experiments.

The irritant effect of the prostaglandin analogues was tested using a behavioural model in cats. In this model the irritant effect on the eye is studied by registering the degree of eyelid closure and the behaviour of the animals. Compounds that cause discomfort and pain in the eye cause the animals to close their eyes. The analogues were applied as carboxylic acid esters, to enhance bioavailability, topically on the eye as a single dose at different dose levels. The animals were then followed for several hours at regular intervals. Each compound and dose was tested on a group of 3–6 cats. At least 3 days elapsed between two consecutive tests on the same animals. An arbitrary scale from 0 (absence of irritation) to 3 (marked irritation), with half steps was used.

Figure 1:
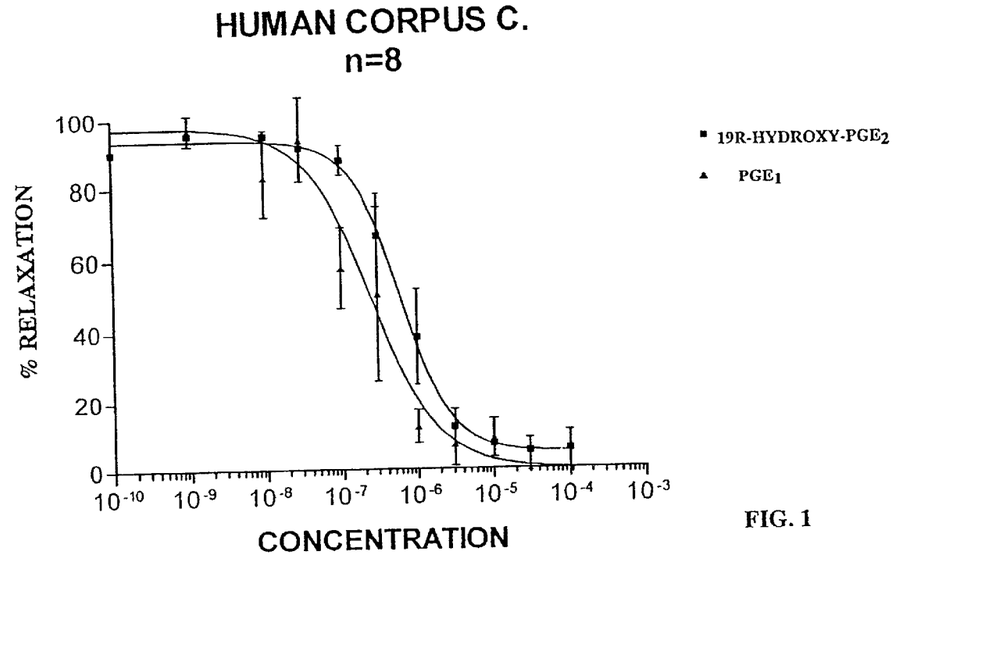
FIG. 1 is a diagram showing the concentration-response relation for $PGE_1$ and 19R-hydroxy-$PGE_2$ in isolated preparation of human corpus cavernosum precontracted with $10^{-6}$ M norepinephrine.

The relaxant effect on the human penile cavernous tissue of $PGE_1$, and 19R-OH-$PGE_2$ are presented in Table I. It can be seen that $PGE_1$ and 19R-OH-$PGE_2$ were about equieffective and comparable to carbachol, however $PGE_1$ was slightly more potent than 19R-OH-$PGE_2$. Since 19R-OH-$PGE_2$ is a selective $EP_2$ receptor agonist this finding indicates that the $EP_2$ receptor accounts for most of the relaxant effect of $PGE_1$. Furthermore, in FIG. 1 it is demonstrated that the concentration-response curves of $PGE_1$ and 19R-OH-$PGE_2$ are parallel and differ only with a factor of about 2–3, i.e. the latter analogue is about half to one third as potent as the former.

TABLE I

Relaxation of human corpus cavernosum tissue induced by prostaglandins compared to carbachol ($10^{-6}$ M). (Mean ± SEM)

| Compound | n | Reduction in tension (%) | EC-50 (Moles/l) |
|---|---|---|---|
| Carbachol | 8 | 100.0 ± 0.0 | — |
| $PGB_i$ | 8 | 90.9 ± 3.7 | $2.5 \times 10^{-7}$ |
| 19R-OH-$PGE_2$ | 8 | 96.9 ± 3.1 | $6.9 \times 10^{-7}$ |

Figure 2:
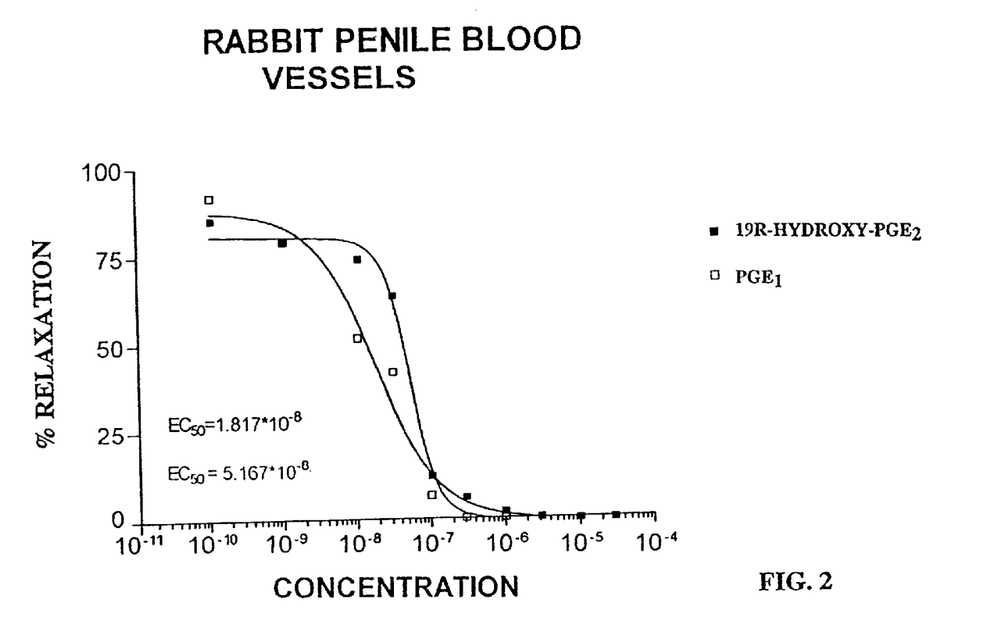
FIG. 2 is a diagram showing the vasodilatory effect of $PGE_1$ and 19R-hydroxy-$PGE_2$ on rabbit penile vasculature precontracted with $10^{-6}$ M norepinephine.

The vasodilatory effect of $PGE_1$ and the $EP_2$ receptor agonist 19R-OH-$PGE_2$ on rabbit penile blood vessels is demonstrated in FIG. 2. It can be seen that the two prostaglandins had the same efficacy in inducing vasodilatation and were also about equipotent. This furthermore demonstrates that the $EP_2$ receptor mediates most of the vasodilatory effect of $PGE_1$. The vasodilatory effect of all the prostaglandin analogues as studied in the rat by investigating the immediate reduction in blood pressure upon intravenous infusion is presented in Table II. As can be seen in the table $PGE_1$ and the three hydroxy-substituted $PGE_2$ analogues effectively reduced the blood pressure in the anaesthetized rat, demonstrating an acute vasodilatory response.

TABLE II

Reduction of blood pressure in anaesthetized rats by prostaglandin analogues with agonistic effect on the $EP_2$ receptor. (n = 3 for each dose; Mean ± SEM)

| Prostaglandin analogue | 2.5–3.5 µg/kg | | 7.5–10 µg/kg | | 25–35 µg/kg | |
|---|---|---|---|---|---|---|
| | Blood pressure o (mmHg) | Reduction (%) | Blood pressure o (mmHg) | Reduction (%) | Blood pressure o (mmHg) | Reduction (%) |
| $PGE_i$ | 114 ± 20 | 13 ± 4 | 105 ± 15 | 35 ± 5 | 103 ± 9 | 52 ± 3 |
| 18RS-OH-$PGE_2$ | 122 ± 28 | 7 ± 3 | 123 ± 33 | 15 ± 3 | 115 ± 32 | 32 ± 2 |
| 19R-OH-$PGE_2$ | 115 ± 14 | 13 ± 10 | 103 ± 12 | 31 ± 3 | 91 ± 9 | 43 ± 6 |
| 20-OH-$PGE_2$ | 91 ± 11 | 26 ± 5 | 85 ± 10 | 38 ± 3 | 91 ± 6 | 44 ± 0 |

Blood pressure o = blood pressure before infusion of prostaglandin analogue.

The irritant effects of the three prostaglandin analogues and $PGE_1$ as studied in the feline eye are presented in Table III. All three hydroxy-substituted $PGE_2$-analogues had significantly less irritant effect than $PGE_1$-isopropyl ester and $PGE_1$ acid. Most surprisingly we found that both 18RS-OH-$PGE_2$-methyl ester and 19R-OH-$PGE_2$-methyl ester had no or markedly reduced irritant effect, even at doses 1000 times higher than $PGE_1$-isopropyl ester. Previously it has been shown that 19R-OH-$PGE_2$ does not cause lid closure in rabbits but induces an irritant effect by inducing swelling of the ocular structures (Hall and Jaitly, 1977). We found no evidence of such irritation in the cat eye with 19R-OH-$PGE_2$ or the other hydroxy-substituted $PGE_2$ analogues.

To confirm that 19R-OH-$PGE_2$-methyl ester, which is more hydrophilic than $PGE_1$-isopropyl ester, indeed penetrates into the cornea and the intraocular parts of the eye we measured the intraocular pressure in 3 cats under local anaesthesia before and 1 hour after topical administration of the prostaglandin to the eye. The intraocular pressure was measured by pneumatonometry. One eye was treated with the test compound and the other eye received the vehicle only. In the eyes treated topically with 19R-OH-$PGE_2$-methyl ester the intraocular pressure decreased from 16.3+/−0.9 mmHg to 12.7+/−1.2 mmHg, whereas it was 16.3+/−0.9 mmHg and 15.7+/−0.7 mmHg in the control eyes at the same time points. It is well known that prostaglandins reduce the intraocular pressure in cats (Bito et al., 1989), and it can thus be taken as an evidence that the drug has penetrated into the eye. Furthermore, from Table III it can also be seen that the $PGE_1$ acid, which is a much less lipophilic compound than the 18-, 19- and 20-hydroxy-substituted $PGE_2$-methyl ester analogues, caused significantly more irritation, and at much lower dose, than the hydroxy-substituted analogues. Thus the absence of pain and irritation after administration of 18RS-OH-$PGE_2$, 19R-OH-$PGE_2$ and 20-OH-$PGE_2$ cannot be explained en the basis of increased hydrophilicity and poor bioavailability. Accordingly, selective $EP_2$ prostanoid receptor agonists seem to be very advantageous in that they exhibit no, or markedly reduced irritant effect.

TABLE III

Maximum irritative effect of prostaglandin analogues as studied in cat eyes.
The log P values were estimated based on thin layer chromatography with $PGF_{2\alpha}$
isopropyl ester as reference (log P 4.5). ie = isopropyl ester, me = methyl ester.
Maximum irritation = 3. Mean ± SEM (n = 3 – 6).

| Analogue | log p-value | Dose: 0.01 μg | Dose: 0.1 μg | Dose: 0.3 μg | Dose: 1 μg | Dose: 3 μg | Dose: 10 μg | Dose: 30 μg | Dose: 100 μg |
|---|---|---|---|---|---|---|---|---|---|
| $PGE_1$-ie | 4.7 | 0.4 ± 0.2 | 1.7 ± 0.3 | 2.8 ± 0.1 | — | — | — | — | — |
| $PGE_1$ acid | 0.7 | — | 0.6 ± 0.1 | — | 1.6 ± 0.2 | — | 3.0 ± 0.0 | — | — |
| 18RS-OH—$PGE_{2\text{-me}}$ | 2.7 | — | — | — | 0.0 ± 0.0 | 0.0 ± 0.0 | 0.0 ± 0.0 | 0.3 ± 0.2 | — |
| 19R-OH—$PGE_{2\text{-me}}$ | 2.5 | — | 0.0 ± 0.0 | — | 0.1 ± 0.1 | — | 0.1 ± 0.1 | — | 0.7 ± 0.4 |
| 20-OH—$PGE_{2\text{-me}}$ | 2.2 | — | — | — | — | 0.5 ± 0.0 | 1.2 ± 0.2 | 1.2 ± 04 | — |

REFERENCES

Bito, L. Z., Camras, C. B., Gum, G. G. et al. (1989). The ocular hypotensive effect and side-effects of prostaglandins on the eyes of experimental animals. In: The ocular effects of prostagandins and other eicosanoids (Eds.: L. Z. Bito and J. Stjernschantz). Alan R Liss Inc. New York Pp: 349–368.

Coleman, R. A., Smith, W. L. and Narumiya, S. (1994). VIII. International Union of Pharmacology classification of prostanoid receptors: Properties, distribution and structure of the receptors and their subtypes. Pharmacological Reviews. 46; 205–229.

Hall, D. W. R. and Jaitly, K. D. (1977) Inflammatory responses of the rabbit eye to prostaglandins. Agents Actions. Suppl. 2: 123–133.

Pada-Nathan, H., Hellstrom, W. G. J., Kaiser, F. E. et al. (1997). Treatment of men with erectile dysfunction with transurethral alprostadil. New Eng. J. Med 336; 1–7.

Taylor, P. L. and Kelly R. W. 1974. 19-hydroxylated E prostaglandins of human semem. Nature. 250; 665–667.

What is claimed is:

1. A method of treating female sexual dysfunction, comprising administering to a human a therapeutically effective and physiologically acceptable amount of a prostaglandin selected from the group consisting of 19-hydroxy-$PGE_2$, 19R-hydroxy-$PGE_2$, 18-hydroxy-$PGE_2$, 20-hydroxy-$PGE_2$, and salts or esters thereof, and 19R-hydroxy-$PGE_2$-methyl ester, and 19R-hydroxy-$PGE_2$-isopropyl ester.

2. The method according to claim 1 wherein the prostaglandin is 19R-hydroxy-$PGE_2$-methyl ester.

3. The method according to claim 1 wherein the prostaglandin is 19R-hydroxy-$PGE_2$-isopropyl ester.

4. The method according to claim 1, 2, or 3 wherein the prostaglandin is administered topically on the female genitals in a form selected from the group consisting of liniment, cream, ointment, gel and solid.

* * * * *